United States Patent
Nanda

(10) Patent No.: US 7,201,172 B2
(45) Date of Patent: Apr. 10, 2007

(54) TOOTHBRUSH HAVING FLOSSING DISPENSER ON HANDLE

(75) Inventor: Puneet Nanda, Cerritos, CA (US)

(73) Assignee: Dr. Fresh, Inc., Buena Park, CA (US)

( * ) Notice: Subject to any disclaimer, the term of this patent is extended or adjusted under 35 U.S.C. 154(b) by 162 days.

(21) Appl. No.: 11/055,664

(22) Filed: Feb. 10, 2005

(65) Prior Publication Data

US 2006/0248670 A1    Nov. 9, 2006

(51) Int. Cl.
*A45D 44/18* (2006.01)
(52) U.S. Cl. ......................... 132/309; 132/311
(58) Field of Classification Search ............... 132/309, 132/311, 323–325, 329
See application file for complete search history.

(56) References Cited

U.S. PATENT DOCUMENTS

| 3,853,134 | A | * | 12/1974 | McCord ..................... 132/309 |
| 3,913,597 | A | * | 10/1975 | Day ........................... 132/324 |
| 4,821,752 | A | * | 4/1989 | Widlak ....................... 132/309 |
| 4,934,389 | A | * | 6/1990 | Pettiford .................... 132/325 |
| 5,607,050 | A | * | 3/1997 | Dolan et al. ............... 206/63.5 |
| 5,865,195 | A | * | 2/1999 | Carter ........................ 132/309 |
| 6,766,807 | B2 | * | 7/2004 | Piccolo et al. ............. 132/309 |
| 2003/0188761 | A1 | * | 10/2003 | Garcia et al. ............... 132/309 |
| 2005/0211263 | A1 | * | 9/2005 | Kuo ........................... 132/310 |

* cited by examiner

*Primary Examiner*—Cary O'Connor
(74) *Attorney, Agent, or Firm*—McKee Voorhees & Sease, P.L.C.

(57) ABSTRACT

A toothbrush includes a handle having first and second ends and a head operatively connected to the second end of the handle. Bristles are on the head; an inner cavity is disposed within the first end of the handle; and dental floss is contained in the cavity. A lid is hinged to the first end of the handle and the lid is comprised of a cover member and a flap member.

15 Claims, 3 Drawing Sheets

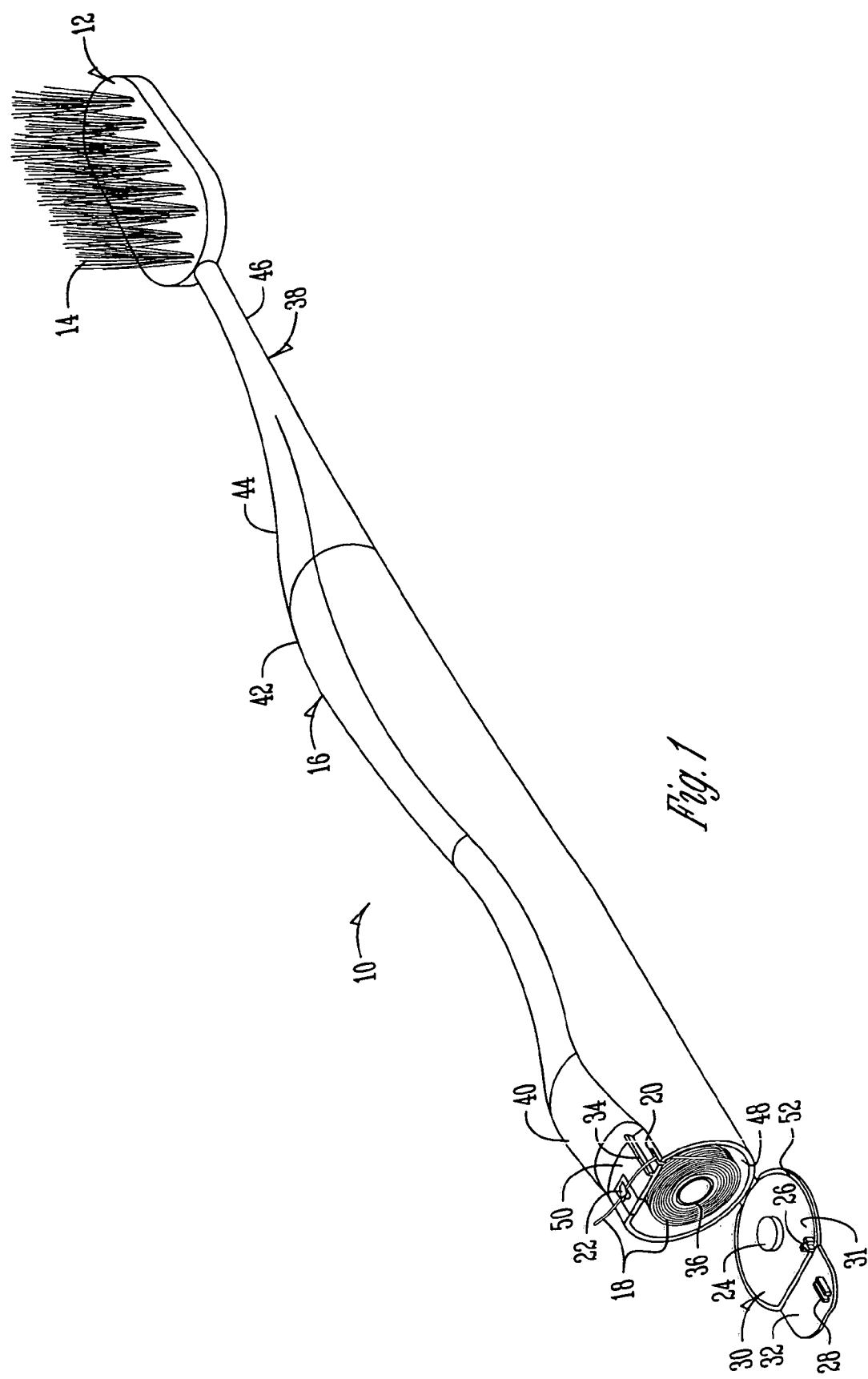

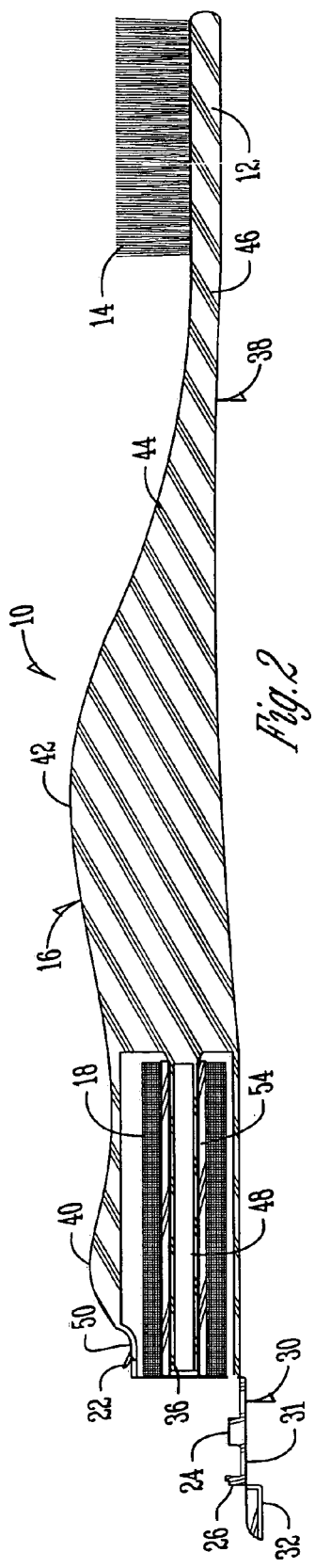
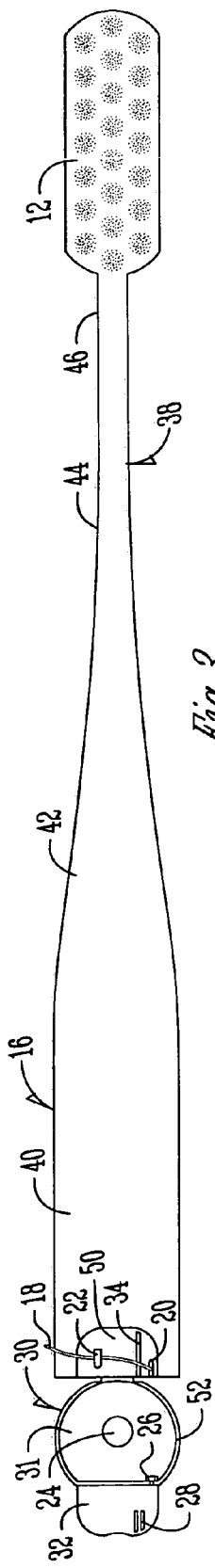
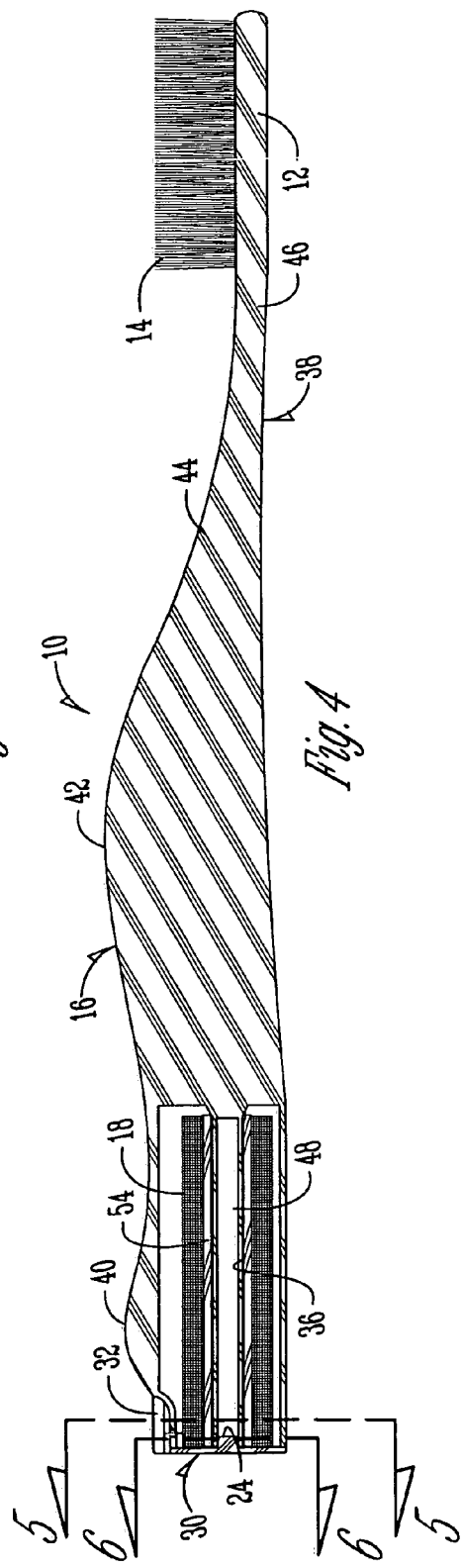

TOOTHBRUSH HAVING FLOSSING DISPENSER ON HANDLE

FIELD OF THE INVENTION

This invention relates to a toothbrush having a flossing dispenser in its handle and to a method of using it.

BACKGROUND OF THE INVENTION

The present invention relates to a toothbrush having a flossing dispenser on the handle. In the design and use of a toothbrush, there is a need for a toothbrush with a flossing dispenser. Brushing and flossing go together in dental care. And, all too often, a floss container cannot be found when it is time to brush. This is especially true if one travels with a brush. Therefore, the primary objective of the present invention is to provide a toothbrush with a flossing dispenser in the handle.

A further objective of the present invention is to provide a device which is easy to use and economical to manufacture.

A further objective of the present invention is to provide a device that is durable and safe in use.

A further objective of the present invention is to promote good dental care.

A further objective of the present invention is to make brushing and flossing convenient by having both the brush and the floss in one apparatus.

A further objective of the present invention is to provide a device where the floss is unobtrusive when the brush is being used.

A further objective of the present invention is to provide a device where the floss can be easily replaced or refilled.

A further objective of the present invention is to provide a device where the floss is enclosed within the handle when the brush is being used.

A further objective of the present invention is to provide a device that includes a cutter for cutting off segments of floss.

A further objective of the present invention is to provide a lid which can be closed during use of the brush but which is easy to open for exposing floss.

A further objective of the present invention is to provide a lid that is bi-folding so that it can be opened to one position for cutting floss segments and opened to a second position for removal of the spool of floss.

A further objective of the present invention is to provide floss that is easily unrolled and cut into segments for use.

The means and method of accomplishing these and other objectives will become apparent from the following description of the invention.

BRIEF SUMMARY OF THE INVENTION

The foregoing objectives may be achieved by a toothbrush for improving dental care. The toothbrush has a flossing dispenser on the handle. The inside of the handle is hollow to incorporate a roll of dental floss. The invention further relates to a method of dispensing floss from such a toothbrush.

In more detail, the toothbrush includes a toothbrush body with a handle having a first end and an opposite second end. The second end of the handle is operatively connected to a first end of a neck and a head is operatively connected to an opposite second end of the neck. A plurality of bristles is attached to the receiving head. The handle has a hand conforming shape for gripping by a user. The handle has a recessed area at the first end of the handle. An inner cavity is disposed within the handle at the first end of the handle. A lid is hinged to the first end of the handle for enclosing or providing access to the inner cavity. A guide slot is cut longitudinally into the first end of the handle within the recessed area. A protruding ridge is also within the recessed area of the handle. A floss cutter is disposed within the recessed area. A lid includes a cover member and a flap member. The flap member is hinged to the cover member. An alignment member protrudes from the cover member such that the alignment member is directed inwardly into the inner cavity when the cover member is in a closed position. A pair of protrusions on the flap member matingly attach to the protruding ridge within the recessed area of the handle. A retaining member protrudes from the cover member such that the retaining member is directed inwardly to rest against the guide slot of the handle when the lid is in a closed position. A lip member protrudes from the cover member. An alignment cylinder is disposed within the inner cavity for accepting a roll of dental floss.

The method of dispensing floss includes providing a toothbrush body having a hollow first end of a handle for receiving a roll of dental floss and an opposite second end of the handle. A roll of floss is inserted into the hollow first end of the handle to retain the roll of floss. The floss is threaded through the guide slot and then the cover member is closed. The floss is then pulled over the ridge to the floss cutter where the floss is secured and the extra floss is cut-off. The flap member of the toothbrush is closed.

BRIEF DESCRIPTION OF THE DRAWINGS

FIG. 1 is an isometric view of a toothbrush with the floss dispenser open.

FIG. 2 is a cross-sectional side view of a toothbrush showing the inner cavity where the roll of floss sits and with the lid open.

FIG. 3 is a top view of a toothbrush showing the guide slot, ridge and floss cutter with the lid open.

FIG. 4 is a cross-sectional side view of a toothbrush showing the inner cavity where the roll of floss sits and with the lid closed.

DETAILED DESCRIPTION OF THE PREFERRED EMBODIMENT

Figure 5:
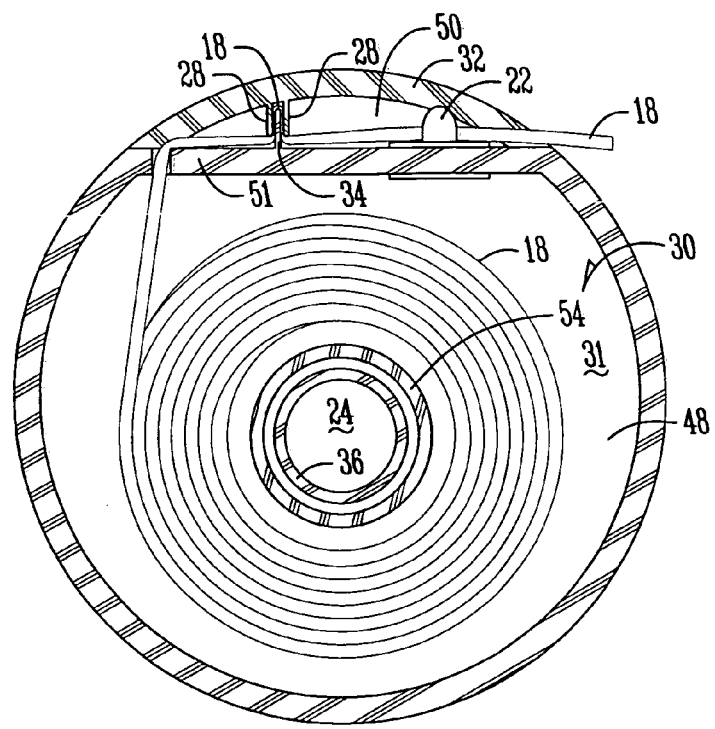
FIG. 5 is a sectional view taken along line 5—5 of FIG. 4.

Referring to FIG. 1, an isometric view, 10 generally refers to the toothbrush of the present invention. The handle 16 of the toothbrush is where the toothbrush is gripped. The handle 16 has a hand conforming shape for gripping by a user. The first end of the handle is 40 while the second end of the handle is 42. The handle 16 connects to the neck 38. The handle 16 and neck 38 are preferably of one piece construction. The first end of the neck is 44 and the second end of the neck is 46. Attached to the second end of the neck 46 is the toothbrush head 12 containing bristles 14. The bristles 14 are for cleaning teeth. The first end of the handle 40 is hollow and contains a roll of dental floss 18. The dental floss 18 unrolls and goes through the guide slot 20 over the ridge 34 and onto the floss cutter 22 where it is cut into lengths. The guide slot 20 aligns the floss 18 after coming off a roll. The ridge 34 separates the floss 18 from the handle 16 making it easier to grab. The floss cutter 22 both cuts the floss and keeps the loose end. There is a cover member 31 for covering the dental floss 18 and a flap member 32 for covering the guide slot 20, ridge 34 and floss cutter 22. The flap member 32 is openable with a thumb. The cover member 31 is openable by pulling on the flap member 32. The cover member 31 closes with the retaining member 26 attaching to the guide slot 20. The retaining member 26 only attaches to the top of the guide slot 20 leaving room at the bottom for the floss 18. The flap member 32 closes with the pair of protrusions 28 that straddle the ridge 34. On the cover member 31 is the male alignment cylinder 24 that, when the cover member 31 is closed, fits into the female alignment cylinder 36. The male alignment cylinder 24 has a smaller diameter than the female alignment cylinder 36 and snaps into place. The alignment cylinders keep the roll of dental floss 18 centered and unrolling smoothly. The dental floss 18 is available with only the flap member 32 opened. Only when the dental floss 18 needs changing does the cover member need to be opened. The lid 30 incorporates both the cover member 31 and the flap member 32. The floss 18 fits within the inner cavity 48.

Referring to FIG. 2, a side cross-sectional view, the hollow end 40 of the toothbrush 10 includes an inner cavity 48 where the roll of dental floss 18 goes. Inner cavity 48 includes a female alignment cylinder 36 which fits within the cylindrical core 54 of the roll of dental floss 18. The dental floss 18 is wrapped around the cylindrical core 54. Detail is shown in the cover member 31 and flap member 32 which together comprise a bifolding lid 30. The retaining member 26 and male alignment cylinder 24 (short) are shown in their open positions. The inner cavity 48 can extend well into the toothbrush handle. This side view shows the recessed area 50 of the handle including the floss cutter 22.

Referring to FIG. 3, a top view, the cover member 31 and flap member 32 are shown. Attached to the flap member 32 are the pair of protrusions 28; attached to the cover member 31 is the retaining member 26. Recess 50 includes the guide slot 20 for the dental floss 18, and the ridge 34 and the floss cutter 22. Also shown are the lip member 52 and the recessed area of the handle 50.

FIG. 4 is a side cross-sectional view the same as FIG. 2 except the cover member 31 and flap member 32 are in their closed positions and the male alignment cylinder 24 is inserted into the female alignment cylinder 36. In this position of lid 30, the pair of protrusions 28 embrace the ridge 34 to provide a snap attachment of flap member 32 to the recessed area 50.

Referring to FIG. 5, the floss 18 is inside the toothbrush inner cavity 48 looking towards the cover member 31. The floss cutter 22 is adapted to cut floss 18, and the pair of protrusions 28 embrace the ridge 34.

Figure 6:
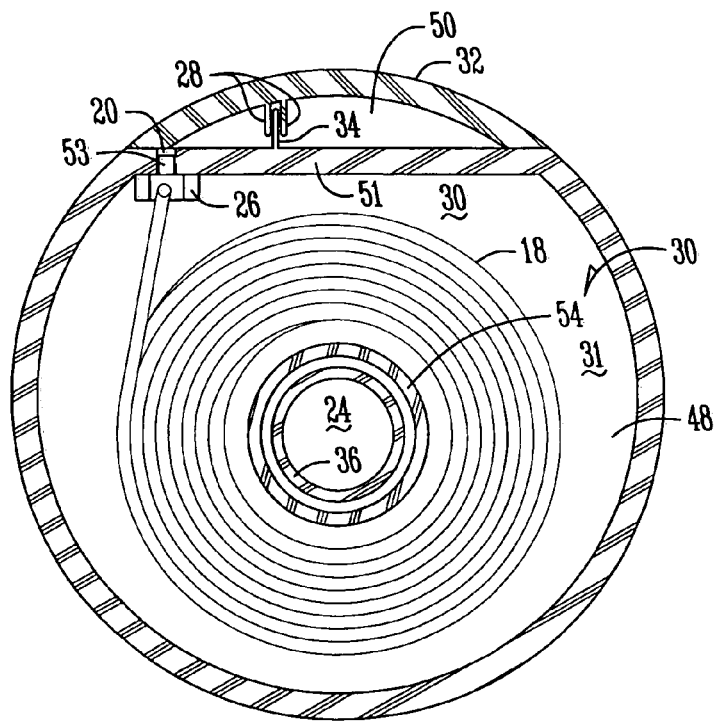
FIG. 6 is a sectional view taken along line 6—6 of FIG. 4.

Referring to FIG. 6, the floss 18 is inside the toothbrush inner cavity 48 and the retaining member 26 tightly fits against the lower wall 51 of recess 50 to secure the lid 30 in its closed position. Retaining member 26 includes a ridge 53 that frictionally fits within a slot 20 in lower wall 51.

The method of using the toothbrush having a flossing dispenser on the brush handle 16 is as follows. Insert the floss 18 onto a female alignment cylinder 36 in the hollow first end of the handle 40. The floss 18 is threaded through guide slot 20 and then outwardly from the first end of the handle 40. The cover member 31 is closed, but the flap 32 is open. The floss 18 is pulled out to a length appropriate for flossing. Floss cutter 22 is then used to cut the floss 18 to length.

The floss 18 continues to unroll until all the floss 18 is gone, leaving only the cylindrical core 54. The core 54 is removed by unsnapping cover member 31 and is replaced by a new roll of floss 18 on a new core 54. Cover member 31 is then snapped back in place.

In the drawings and specifications there has been set forth a preferred embodiment of the invention, and although specific terms are employed, their use is in a generic descriptive sense only and not for purposes of limitation. Changes in the form and the proportion of parts as well as in the substitution of equivalents are contemplated as circumstance may suggest or render expedient. For example, the present invention contemplates that the handle can be of various shapes or materials. The handle is preferably plastic or rubber coated plastic, but can also be wood or metal. The bristles are preferably nylon, but can be made of different materials. These and other variations are well within the spirit or scope of the invention in the following claims.

What is claimed is:

1. A toothbrush for improving dental care, comprising:
   a handle having opposite first and second ends;
   a head operatively connected to the second end of the handle;
   a plurality of bristles on the head;
   an inner cavity disposed within the first end of the handle;
   floss material contained in the cavity;
   a lid hinged to the first end of the handle for movement between open and closed positions relative to the cavity, the lid including a cover member and a flap member, the flap member hinged to the cover member.

2. The toothbrush of claim 1 further comprising a recess in the first end of the handle.

3. The toothbrush of claim 1 further comprising a slot in the first end of the handle through which floss material extends.

4. The toothbrush of claim 1 further comprising a protruding ridge on the first end of the handle.

5. The toothbrush of claim 1 further comprising a floss cutter disposed on the first end of the handle.

6. The toothbrush of claim 1 wherein the lid includes an alignment member protruding from the cover member such that the alignment member is directed inwardly into the inner cavity when the cover member is in the closed position.

7. The toothbrush of claim 1 wherein the lid includes a pair of protrusions on the flap member.

8. The toothbrush of claim 1 wherein the lid includes a retaining member protruding from the cover member such that the retaining member engages the slot of the handle when the cover member is in a closed position.

9. The toothbrush of claim 1 wherein the lid includes a lip member protruding from the cover member to mate with the first end of the handle when the cover member is in the closed position.

10. The toothbrush of claim 1 further comprising a cylinder disposed within the inner cavity for mounting a roll of the floss material.

11. An improved toothbrush, comprising:
    a handle having a first end and an opposite second end, the second end of the handle operatively connected to a first end of a neck and a head operatively connected to an opposite second end of the neck;
    a plurality of bristles attached to the head;
    an inner cavity disposed within the handle at the first end of the handle;

a lid hinged to the first end of the handle for enclosing or providing access to the inner cavity;
a slot extending into the first end of the handle;
a floss cutter positioned proximate to the slot;
the lid comprising:
(a) a cover member and a flap member, the flap member hinged to the cover member;
(b) a lip member protruding from the cover member.

12. The toothbrush of claim 11 further comprising an alignment member protruding from the cover member such that the alignment member is directed inwardly into the inner cavity when the cover member is in a closed position.

13. The toothbrush of claim 11 further comprising a pair of protrusions on the flap member for matingly attaching to a protruding ridge within a recessed area of the handle.

14. The toothbrush of claim 11 further comprising a retaining member protruding from the cover member such that the retaining member engages the slot of the handle when the cover member is in a closed position.

15. The toothbrush of claim 11 further comprising a cylinder disposed within the inner cavity for mounting a roll of dental floss.

* * * * *